United States Patent
Kanai et al.

(10) Patent No.: US 9,796,677 B2
(45) Date of Patent: Oct. 24, 2017

(54) AMIDE COMPOUND AND PHARMACEUTICAL COMPRISING SAME

(71) Applicant: JAPAN SCIENCE AND TECHNOLOGY AGENCY, Kawaguchi-shi (JP)

(72) Inventors: Motomu Kanai, Bunkyo-ku (JP); Yohei Soma, Bunkyo-ku (JP); Tadamasa Arai, Fujisawa (JP); Takushi Araya, Katsushika-ku (JP)

(73) Assignee: JAPAN SCIENCE AND TECHNOLOGY AGENCY, Kawaguchi-shi (JP)

( * ) Notice: Subject to any disclaimer, the term of this patent is extended or adjusted under 35 U.S.C. 154(b) by 0 days.

(21) Appl. No.: 15/100,866

(22) PCT Filed: Dec. 9, 2014

(86) PCT No.: PCT/JP2014/082521
§ 371 (c)(1),
(2) Date: Jun. 1, 2016

(87) PCT Pub. No.: WO2015/087865
PCT Pub. Date: Jun. 18, 2015

(65) Prior Publication Data
US 2016/0297764 A1    Oct. 13, 2016

(30) Foreign Application Priority Data

Dec. 10, 2013  (JP) .................. 2013-254908
May 30, 2014  (JP) .................. 2014-112179

(51) Int. Cl.
*A61K 31/44*   (2006.01)
*A61K 31/505*  (2006.01)
*C07D 213/81*  (2006.01)
*C07D 239/28*  (2006.01)
*C07D 239/30*  (2006.01)

(52) U.S. Cl.
CPC ......... *C07D 213/81* (2013.01); *C07D 239/30* (2013.01)

(58) Field of Classification Search
CPC .... A61K 31/44; A61K 31/505; C07D 213/81; C07D 239/28
USPC ........ 514/256, 269, 348, 349, 350; 544/319, 544/329, 335; 546/296, 297, 298
See application file for complete search history.

(56) References Cited

U.S. PATENT DOCUMENTS

2004/0171881 A1   9/2004  John et al.
2007/0088165 A1   4/2007  Nantermet et al.
2008/0015233 A1   1/2008  Barrow et al.

FOREIGN PATENT DOCUMENTS

JP     2005-520791 A    7/2005
JP     2007-515404 A    6/2007
JP     2007-533757 A   11/2007
WO  WO 03/040096 A2    5/2003

OTHER PUBLICATIONS

International Search Report dated Jan. 20, 2015, in PCT/JP2014/082521 filed Dec. 9, 2014.
J. Hardy, et al., "The Amyloid Hypothesis of Alzheimer's Disease: Progress and Problems on the Road to Therapeutics", Science, vol. 297, (Jul. 2002), 6 pages.
S. A. Gravina et al., "Communication; Amyloid β Protein (Aβ) in Alzheimer's Disease Brain; Biochemical and Immunocytochemical Analysis with Antibodies Specific for Forms Ending at Aβ40 or Aβ42(43)", The Journal of Biological Chemistry., vol. 270, No. 13, (1995), pp. 7013-7016.
L. O. Tjernberg et al., Communication; Arrest of β-Amyloid Fibril Formation by a Pentapeptide Ligand, The Journal of Biological Chemistry, vol. 271, No. 15, (1996), pp. 8545-8548.
Arai, T. et al., "Rational Design and Identification of a Non-Peptidic Aggregation Inhibitor of Amyloid-β Based on a Pharmacophore Motif Obtained from cyclo[-Lys-Leu-Val-Phe-Phe-]", Angewandte Communications, International Edition, Amyloid Inhibitors Hot Paper, vol. 53, No. 31, (Jun. 2014), pp. 8236-8239.
Extended European Search Report dated May 9, 2017 in Patent Application No. 14870019.8.
Cliff I. Stains, et al., "Molecules That Target beta-Amyloid" ChemMedChem, vol. 2, No, 12, XP009107501, 2007, pp. 1674-1692.

*Primary Examiner* — Brenda Coleman
(74) *Attorney, Agent, or Firm* — Oblon, McClelland, Maier & Neustadt, L.L.P.

(57) ABSTRACT

Provided is a novel compound which has an excellent Aβ aggregation inhibitory effect and is useful as a pharmaceutical. An amide compound represented by the formula (1) or a salt thereof, wherein Z represents CH or N; A and B are the same or different and each represents —$CH_2$—, —O—, —S—, or —NH—; $R^1$ and $R^2$ are the same or different and each represents a branched alkyl group, a branched alkenyl group, an optionally substituted aromatic hydrocarbon group, an optionally substituted aralkyl group, an optionally substituted cycloalkyl group, or an optionally substituted aromatic heterocyclic group; and $R^3$ represents a branched alkyl group, a branched alkenyl group, an optionally substituted cycloalkyl group, or an optionally substituted aralkyl group.

(1)

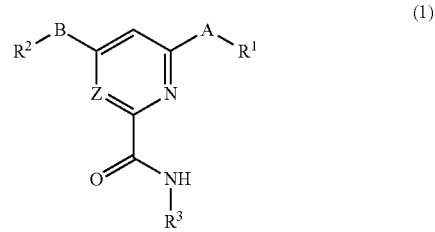

20 Claims, No Drawings

AMIDE COMPOUND AND PHARMACEUTICAL COMPRISING SAME

FIELD OF THE INVENTION

The present invention relates to an amide compound and a pharmaceutical for the prevention or treatment of diseases involving amyloid deposition, for example, Alzheimer's disease, comprising the same.

BACKGROUND OF THE INVENTION

Alzheimer's disease is a neurodegenerative disease pathologically characterized by neuronal degeneration and loss as well as formation of senile plaques and neurofibrillary tangles. Alzheimer's disease causes cognitive symptoms which progressively destroy memory, recognition, thinking, judgment, and the like, eventually leading to death.

A principal protein constituting the senile plaques deposited in the brain is amyloid β peptide (Aβ), which consists of 39 to 43 amino acids. Aβ exhibits cytotoxicity, and this cytotoxicity is considered to cause Alzheimer's disease (Non Patent Literature 1). Aβ secreted from cells is a polypeptide consisting mainly of 40 or 42 amino acids. Particularly, Aβ consisting of 42 amino acids is known to have a stronger aggregability leading to its earlier deposition in the brain, and stronger cytotoxicity (Non Patent Literature 2). Thus, an agent for inhibiting Aβ aggregation has been expected as a prophylactic or therapeutic agent for Alzheimer's disease.

L-[Lys-Leu-Val-Phe-Phe], a partial sequence of Aβ, is known to have aggregation inhibitory activity against Aβ (Non Patent Literature 3).

CITATION LIST

Non Patent Literature

Non Patent Literature 1: J. Hardy, D. J. Selkoe, Science 2002, 297, p. 353
Non Patent Literature 2: J. Biol. Chem., 1995, Vol. 270, p. 7013
Non Patent Literature 3: J. Biol. Chem., 1996, Vol. 271, p. 8545

SUMMARY OF THE INVENTION

Problems to be Solved by the Invention

The Aβ aggregation inhibitory activity of the pentapeptide described above, however, is very weak. In addition, this pentapeptide consists of naturally occurring amino acids. Therefore, its low metabolic stability is of concern.

Thus, an object of the present invention is to provide a novel compound which has an excellent Aβ aggregation inhibitory effect and is useful as a pharmaceutical.

Means for Solving the Problems

Accordingly, the present inventors used the pentapeptide as a control and conducted various studies to find a low-molecular compound having better Aβ aggregation inhibitory activity than that of this pentapeptide. As a result, the present inventors found that an amide compound represented by the formula (1) given below or a salt thereof has excellent Aβ aggregation inhibitory activity and is useful as a prophylactic or therapeutic agent for various diseases caused by amyloid deposition, for example, Alzheimer's disease, and completed the present invention on the basis of this finding.

Specifically, the present invention provides the following [1] to [17]:

[1] An amide compound represented by the formula (1) or a salt thereof:

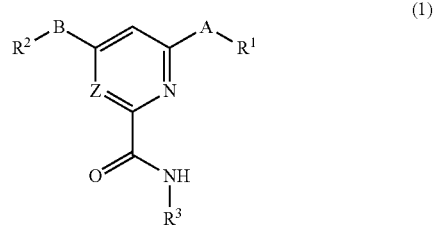

(1)

wherein
Z represents CH or N;
A and B are the same or different and each represents —$CH_2$—, —O—, —S—, or —NH—;
$R^1$ and $R^2$ are the same or different and each represents a branched alkyl group, a branched alkenyl group, an optionally substituted aromatic hydrocarbon group, an optionally substituted aralkyl group, an optionally substituted cycloalkyl group, or an optionally substituted aromatic heterocyclic group; and
$R^3$ represents a branched alkyl group, a branched alkenyl group, an optionally substituted cycloalkyl group, or an optionally substituted aralkyl group.

[2] The amide compound according to [1] or a salt thereof, wherein A and B are the same or different and each is —$CH_2$— or —O—.

[3] The amide compound according to [1] or [2] or a salt thereof, wherein A is —$CH_2$— or —O—, and B is —$CH_2$—.

[4] The amide compound according to any of [1] to [3] or a salt thereof, wherein A is —O—, and B is —$CH_2$—.

[5] The amide compound according to any of [1] to [4] or a salt thereof, wherein $R^1$ and $R^2$ are the same or different and each is a branched alkyl group having 3 to 12 carbon atoms, a branched alkenyl group having 3 to 12 carbon atoms, an optionally substituted aromatic hydrocarbon group having 6 to 14 carbon atoms, an optionally substituted aralkyl group having 7 to 18 carbon atoms, or an optionally substituted cycloalkyl group having 3 to 12 carbon atoms; and $R^3$ is a branched alkyl group having 3 to 12 carbon atoms, a branched alkenyl group having 3 to 12 carbon atoms, an optionally substituted cycloalkyl group having 3 to 12 carbon atoms, or an optionally substituted aralkyl group having 6 to 18 carbon atoms.

[6] The amide compound according to any of [1] to [5] or a salt thereof, wherein $R^1$ and $R^2$ are the same or different and each is an optionally substituted aromatic hydrocarbon group having 6 to 14 carbon atoms, an optionally substituted aralkyl group having 7 to 18 carbon atoms, or an optionally substituted cycloalkyl group having 3 to 12 carbon atoms; and $R^3$ is a branched alkyl group having 3 to 12 carbon atoms, a branched alkenyl group having 3 to 12 carbon atoms, an optionally substituted cycloalkyl group having 3 to 12 carbon atoms, or an optionally substituted aralkyl group having 6 to 18 carbon atoms.

[7] The amide compound according to any of [1] to [6] or a salt thereof, wherein $R^1$ and $R^2$ are the same or different and each is a branched alkyl group having 3 to 12 carbon atoms, a branched alkenyl group having 3 to 12 carbon atoms, an optionally substituted aromatic hydrocarbon group having 6 to 14 carbon atoms, an optionally substituted aralkyl group having 7 to 18 carbon atoms, or an optionally substituted cycloalkyl group having 3 to 12 carbon atoms; and $R^3$ is a branched alkyl group having 3 to 12 carbon atoms, a branched alkenyl group having 3 to 12 carbon atoms, an optionally substituted cycloalkyl group having 3 to 12 carbon atoms, or an optionally substituted aralkyl group having 6 to 18 carbon atoms, wherein the group(s) capable of substituting the aromatic hydrocarbon group, the aralkyl group, or the cycloalkyl group is 1 to 5 groups selected from the group consisting of an alkyl group having 1 to 4 carbon atoms, an alkoxy group having 1 to 4 carbon atoms, a hydroxy group, a halogen atom, a nitro group, an amino group, a mono-$C_{1-4}$ alkylamino group, a di-$C_{1-4}$ alkylamino group, and a halogeno-$C_{1-4}$ alkyl group.

[8] The amide compound according to any of [1] to [7] or a salt thereof, wherein $R^1$ and $R^2$ are the same or different and each is an optionally substituted aromatic hydrocarbon group having 6 to 14 carbon atoms, an optionally substituted aralkyl group having 7 to 18 carbon atoms, or an optionally substituted cycloalkyl group having 3 to 12 carbon atoms; and $R^3$ is a branched alkyl group having 3 to 12 carbon atoms, a branched alkenyl group having 3 to 12 carbon atoms, an optionally substituted cycloalkyl group having 3 to 12 carbon atoms, or an optionally substituted aralkyl group having 6 to 18 carbon atoms, wherein the group(s) capable of substituting the aromatic hydrocarbon group, the aralkyl group, or the cycloalkyl group is 1 to 5 groups selected from the group consisting of an alkyl group having 1 to 4 carbon atoms, an alkoxy group having 1 to 4 carbon atoms, a hydroxy group, a halogen atom, a nitro group, an amino group, a mono-$C_{1-4}$ alkylamino group, a di-$C_{1-4}$ alkylamino group, and a halogeno-$C_{1-4}$ alkyl group.

[9] An amyloid β peptide aggregation inhibitor comprising an amide compound according to any of [1] to [8] or a salt thereof as an active ingredient.

[10] A pharmaceutical comprising an amide compound according to any of [1] to [8] or a salt thereof.

[11] The pharmaceutical according to [10], which is a prophylactic or therapeutic agent for Alzheimer's disease.

[12] A pharmaceutical composition comprising an amide compound according to any of [1] to [8] or a salt thereof and a pharmaceutically acceptable carrier.

[13] The pharmaceutical composition according to [12], which is a pharmaceutical composition for the prevention or treatment of Alzheimer's disease.

[14] Use of an amide compound according to any of [1] to [8] or a salt thereof for the production of an amyloid β peptide aggregation inhibitor.

[15] Use of an amide compound according to any of [1] to [8] or a salt thereof for the production of a prophylactic or therapeutic agent for Alzheimer's disease.

[16] The amide compound according to any of [1] to [8] or a salt thereof, for use in inhibiting amyloid β peptide aggregation.

[17] The amide compound according to any of [1] to [8] or a salt thereof, for use in preventing or treating Alzheimer's disease.

[18] A method for inhibiting amyloid β peptide aggregation, comprising administering an amide compound according to any of [1] to [8] or a salt thereof.

[19] A method for preventing or treating Alzheimer's disease, comprising administering an amide compound according to any of [1] to [8] or a salt thereof.

Effects of the Invention

The amide compound represented by the formula (1) or a salt thereof has far superior Aβ aggregation inhibitory activity and is useful as a pharmaceutical for the prevention or treatment of diseases caused by amyloid deposition, for example, Alzheimer's disease and Down syndrome.

MODES FOR CARRYING OUT THE INVENTION

In the formula (1), Z represents CH or N. When Z is CH, the compound of the formula (1) is a picolinic acid amide. When Z is N, the compound of the formula (1) is a pyrimidine-2-carboxamide.

In the formula (1), A and B are the same or different and each represents —$CH_2$—, —O—, —S—, or —NH—. Among others, A and B are the same or different and each is preferably —$CH_2$—, —O—, or —S—, more preferably —$CH_2$— or —O—. More preferably, A is —$CH_2$— or —O—, and B is —$CH_2$—. Even more preferably A is —O—, and B is —$CH_2$—.

In the formula (1), $R^1$ and $R^2$ are the same or different and each represents a branched alkyl group, a branched alkenyl group, an optionally substituted aromatic hydrocarbon group, an optionally substituted aralkyl group, an optionally substituted cycloalkyl group, or an optionally substituted aromatic heterocyclic group. $R^3$ represents a branched alkyl group, a branched alkenyl group, an optionally substituted cycloalkyl group, or an optionally substituted aralkyl group.

The branched alkyl group represented by $R^1$, $R^2$, or $R^3$ is preferably a branched alkyl group having 3 to 12 carbon atoms, more preferably a branched alkyl group having 3 to 8 carbon atoms. Specific examples of the branched alkyl group include an isopropyl group, an isobutyl group, a sec-butyl group, a tert-butyl group, an isopentyl group, an isohexyl group, an isoheptyl group, an isooctyl group, and a 2-ethylhexyl group.

The branched alkenyl group represented by $R^1$, $R^2$, or $R^3$ is preferably a branched alkenyl group having 3 to 12 carbon atoms, more preferably a branched alkenyl group having 3 to 8 carbon atoms. Specific examples of the branched alkenyl group include an isopropenyl group, an isobutenyl group, an isopentenyl group, and an isohexenyl group.

The optionally substituted aromatic hydrocarbon group represented by $R^1$, $R^2$, or $R^3$ is preferably an optionally substituted aromatic hydrocarbon group having 6 to 14 carbon atoms. In this context, examples of the aromatic hydrocarbon group having 6 to 14 carbon atoms include a phenyl group, an indenyl group, a naphthyl group, a biphenyl group, a phenanthrenyl group, and an anthracenyl group. Among these groups, a phenyl group, a naphthyl group, or a biphenyl group is more preferred.

Examples of the group(s) capable of substituting the aromatic hydrocarbon group include 1 to 5 groups selected from the group consisting of an alkyl group having 1 to 4 carbon atoms, an alkoxy group having 1 to 4 carbon atoms, a hydroxy group, a halogen atom, a nitro group, an amino group, a mono-$C_{1-4}$ alkylamino group, a di-$C_{1-4}$ alkylamino group, and a halogeno-$C_{1-4}$ alkyl group. In this context, examples of the alkyl group having 1 to 4 carbon atoms include a methyl group, an ethyl group, a n-propyl group, an isopropyl group, a n-butyl group, an isobutyl group, a sec-butyl group, and a tert-butyl group. Examples of the alkoxy group having 1 to 4 carbon atoms include a methoxy group, an ethoxy group, a n-propyloxy group, an isopropyloxy group, and a n-butyloxy group. Examples of the halogen atom include a fluorine atom, a chlorine atom, a bromine atom, and an iodine atom. Examples of the mono-$C_{1-4}$ alkylamino group include a methylamino group, an ethylamino group, and an isopropylamino group. Examples of the di-$C_{1-4}$ alkylamino group include a dimethylamino group, a diethylamino group, and a diisopropylamino group. Examples of the halogeno-$C_{1-4}$ alkyl group include a chloromethyl group, a trichloromethyl group, and a trifluoromethyl group.

The optionally substituted aralkyl group represented by $R^1$, $R^2$, or $R^3$ is preferably an optionally substituted aralkyl group having 7 to 18 carbon atoms, more preferably an optionally substituted aryl-$C_{1-4}$ alkyl group having 6 to 14 carbon atoms.

Examples of the aralkyl group include a phenyl-$C_{1-4}$ alkyl group, an indenyl-$C_{1-4}$ alkyl group, a naphthyl-$C_{1-4}$ alkyl group, and a biphenyl-$C_{1-4}$ alkyl group. Specific examples of the aralkyl group include a benzyl group, a phenylethyl group, a naphthylmethyl group, a naphthylethyl group, a biphenylmethyl group, and a biphenylethyl group.

Examples of the group(s) capable of substituting the aralkyl group include 1 to 5 groups selected from the group consisting of an alkyl group having 1 to 4 carbon atoms, an alkoxy group having 1 to 4 carbon atoms, a hydroxy group, a halogen atom, a nitro group, an amino group, a mono-$C_{1-4}$ alkylamino group, a di-$C_{1-4}$ alkylamino group, and a halogeno-$C_{1-4}$ alkyl group. Specific examples of these substituents are the same as in the substituents on the aromatic hydrocarbon described above.

The optionally substituted cycloalkyl group represented by $R^1$, $R^2$, or $R^3$ is preferably an optionally substituted cycloalkyl group having 3 to 12 carbon atoms.

Examples of the cycloalkyl group include: monocyclic cycloalkyl groups such as a cyclopropyl group, a cyclobutyl group, a cyclopentyl group, a cyclohexyl group, a cycloheptyl group, and a cyclooctyl group; and polycyclic cycloalkyl groups such as a bicyclo[2.2.1]heptanyl group, a bicyclo[3.2.1]octanyl group, a bicyclo[3.3.1]nonanyl group, a noradamantyl group, an adamantyl group, and a homoadamantyl group.

Examples of the group(s) capable of substituting the cycloalkyl group include 1 to 3 groups selected from the group consisting of an alkyl group having 1 to 4 carbon atoms, an alkoxy group having 1 to 4 carbon atoms, a hydroxy group, a halogen atom, a nitro group, an amino group, a mono-$C_{1-4}$ alkylamino group, a di-$C_{1-4}$ alkylamino group, and a halogeno-$C_{1-4}$ alkyl group. Specific examples of these substituents are the same as in the substituents on the aromatic hydrocarbon described above.

Examples of the optionally substituted aromatic heterocyclic group represented by $R^1$, $R^2$, or $R^3$ include an optionally substituted aromatic heterocyclic group having 1 to 3 heteroatoms selected from the group consisting of a nitrogen atom, an oxygen atom, and a sulfur atom. An optionally substituted aromatic heterocyclic group having 2 to 9 carbon atoms in total and having 1 to 3 heteroatoms selected from the group consisting of a nitrogen atom, an oxygen atom, and a sulfur atom is preferred. Specific examples of the aromatic heterocyclic group include a pyrrolyl group, a furanyl group, a thienyl group, an imidazolyl group, an oxazolyl group, a thiazolyl group, a triazinyl group, a pyridyl group, a pyrimidinyl group, an indolyl group, and a benzimidazolyl group. The aromatic heterocyclic group is preferably a pyrrolyl group, a furanyl group, a thienyl group, an imidazolyl group, an oxazolyl group, a thiazolyl group, a pyridyl group, a pyrimidinyl group, or an indolyl group, more preferably an imidazolyl group or a pyridyl group.

Examples of the group(s) capable of substituting the aromatic heterocyclic group include 1 to 5 groups selected from the group consisting of an alkyl group having 1 to 4 carbon atoms, an alkoxy group having 1 to 4 carbon atoms, a hydroxy group, a halogen atom, a nitro group, an amino group, a mono-$C_{1-4}$ alkylamino group, a di-$C_{1-4}$ alkylamino group, and a halogeno-$C_{1-4}$ alkyl group. Specific examples of these substituents are the same as in the substituents on the aromatic hydrocarbon described above.

In the formula (1), preferably, $R^1$ and $R^2$ are the same or different and each is a branched alkyl group having 3 to 12 carbon atoms, a branched alkenyl group having 3 to 12 carbon atoms, an optionally substituted aromatic hydrocarbon group having 6 to 14 carbon atoms, an optionally substituted aralkyl group having 7 to 18 carbon atoms, or an optionally substituted cycloalkyl group having 3 to 12 carbon atoms; and $R^3$ is a branched alkyl group having 3 to 12 carbon atoms, a branched alkenyl group having 3 to 12 carbon atoms, an optionally substituted cycloalkyl group having 3 to 12 carbon atoms, or an optionally substituted aralkyl group having 6 to 18 carbon atoms. In this context, the group(s) capable of substituting the aromatic hydrocarbon group, the aralkyl group, or the cycloalkyl group is preferably 1 to 5 groups selected from the group consisting of an alkyl group having 1 to 4 carbon atoms, an alkoxy group having 1 to 4 carbon atoms, a hydroxy group, a halogen atom, a nitro group, an amino group, a mono-$C_{1-4}$ alkylamino group, a di-$C_{1-4}$ alkylamino group, and a halogeno-$C_{1-4}$ alkyl group.

Also preferably, $R^1$ and $R^2$ are the same or different and each is an optionally substituted aromatic hydrocarbon group having 6 to 14 carbon atoms, an optionally substituted aralkyl group having 7 to 18 carbon atoms, or an optionally substituted cycloalkyl group having 3 to 12 carbon atoms; and $R^3$ is a branched alkyl group having 3 to 12 carbon atoms, a branched alkenyl group having 3 to 12 carbon atoms, an optionally substituted cycloalkyl group having 3 to 12 carbon atoms, or an optionally substituted aralkyl group having 6 to 18 carbon atoms. In this context, the group(s) capable of substituting the aromatic hydrocarbon group, the aralkyl group, or the cycloalkyl group is preferably 1 to 5 groups selected from the group consisting of an alkyl group having 1 to 4 carbon atoms, an alkoxy group having 1 to 4 carbon atoms, a hydroxy group, a halogen atom, a nitro group, an amino group, a mono-$C_{1-4}$ alkylamino group, a di-$C_{1-4}$ alkylamino group, and a halogeno-$C_{1-4}$ alkyl group.

In the formula (1), more preferably, A and B are the same or different and each is —$CH_2$— or —O—; $R^1$ and $R^2$ are the same or different and each is an optionally substituted aromatic hydrocarbon group having 6 to 14 carbon atoms, an optionally substituted aralkyl group having 7 to 18 carbon atoms, or an optionally substituted cycloalkyl group having 3 to 12 carbon atoms; and $R^3$ is a branched alkyl group having 3 to 12 carbon atoms, a branched alkenyl group having 3 to 12 carbon atoms, an optionally substituted cycloalkyl group having 3 to 12 carbon atoms, or an optionally substituted aralkyl group having 6 to 18 carbon atoms. In this context, the group(s) capable of substituting the aromatic hydrocarbon group, the aralkyl group, or the cycloalkyl group is preferably 1 to 5 groups selected from the group consisting of an alkyl group having 1 to 4 carbon atoms, an alkoxy group having 1 to 4 carbon atoms, a hydroxy group, a halogen atom, a nitro group, an amino group, a mono-$C_{1-4}$ alkylamino group, a di-$C_{1-4}$ alkylamino group, and a halogeno-$C_{1-4}$ alkyl group.

Examples of the salt of the amide compound of the formula (1) include pharmaceutically acceptable salts, for example, acid-addition salts including: inorganic acid salts such as hydrochloride, sulfate, nitrate, carbonate, and phosphate; and organic acid salts such as acetate, oxalate, and succinate.

The amide compound of the formula (1) or a salt thereof may have an asymmetric carbon atom. In this case, each optically active form and mixtures thereof are included in the scope of the present invention.

Particularly preferred examples of the amide compound of the present invention or a salt thereof are compounds described in Examples mentioned later or salts thereof.

The amide compound of the present invention or a salt thereof can be produced according to, for example, the following reaction scheme:

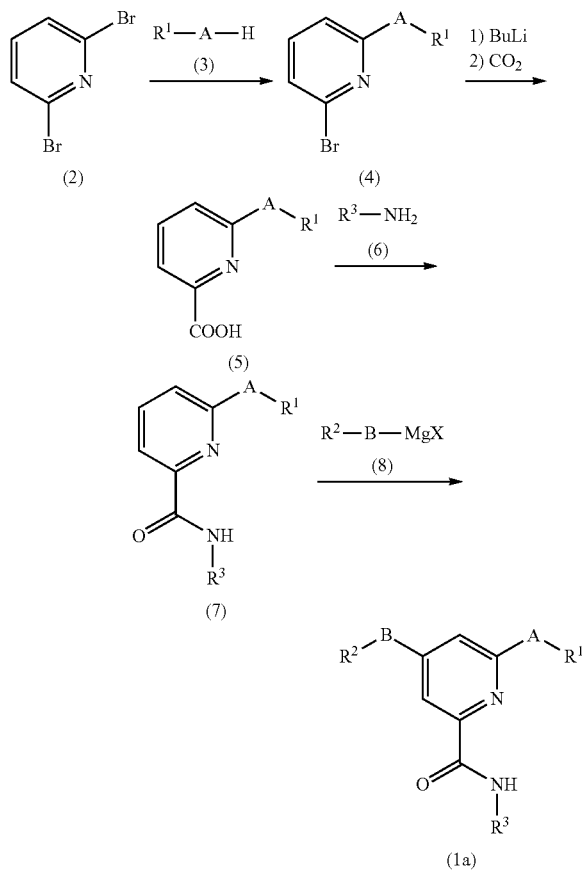

wherein X represents a halogen atom, and $R^1$, $R^2$, $R^3$, A, and B are as defined above.

2,6-Dibromopyridine (2) is reacted with $R^1$-A-H (3) to obtain a compound of the formula (4) (first step); the compound of the formula (4) is reacted with n-BuLi and carbon dioxide to obtain a compound of the formula (5) (second step); the compound of the formula (5) is reacted with $R^3$—$NH_2$ (6) to obtain a compound of the formula (7) (third step); and then, the compound of the formula (7) is reacted with a Grignard reagent (8) to obtain a compound of the formula (1a) (fourth step).

In the first step, for example, $R^1$-A-H (3) is preferably reacted with a base and then reacted with 2,6-dibromobenzene (2). The base is preferably a strong base such as sodium hydride. This reaction can be carried out at room temperature to reflux temperature for 1 to 48 hours in the presence of an amide solvent such as dimethylformamide or dimethylacetamide.

In the second step, first, the compound of the formula (4) is reacted with n-BuLi and subsequently reacted with carbon dioxide. The reaction of the compound of the formula (4) with n-BuLi can be carried out at −80° C. to 0° C. for 5 minutes to 1 hour in an ether solvent such as diethyl ether. Subsequently, the reaction can be carried out for 30 minutes to 5 hours while carbon dioxide is blown into the reaction vessel at a temperature of room temperature to 50° C.

The third step is the step of reacting the compound of the formula (5) with $R^2$—$NH_2$ (6) for amidation. The amidation reaction can be carried out according to ordinary procedures and is preferably carried out in the presence of, for example, a benzotriazole such as 1-hydroxybenzotriazole (HOBt), N-hydroxysuccinimide (HOSu), 1-hydroxybenzotriazole (HOAt), HBTU, or HATU and a condensing agent such as 1-ethyl-3-(3-dimethylaminopropyl)carbodiimide (EDC) or dicyclohexylcarbodiimide.

The fourth step is the step of reacting the compound of the formula (7) with a Grignard reagent ($R^2$=B—MgX (8)) in the presence of a Lewis acid such as $BF_3$, and treating the reaction product with an oxidizing agent such as chloranil to obtain a compound of the formula (1a). The reaction can be carried out at −30° C. to 100° C. for 1 to 20 hours in an ether solvent such as tetrahydrofuran.

Alternatively, the amide compound (1) of the present invention or a salt thereof can also be produced according to the following reaction scheme:

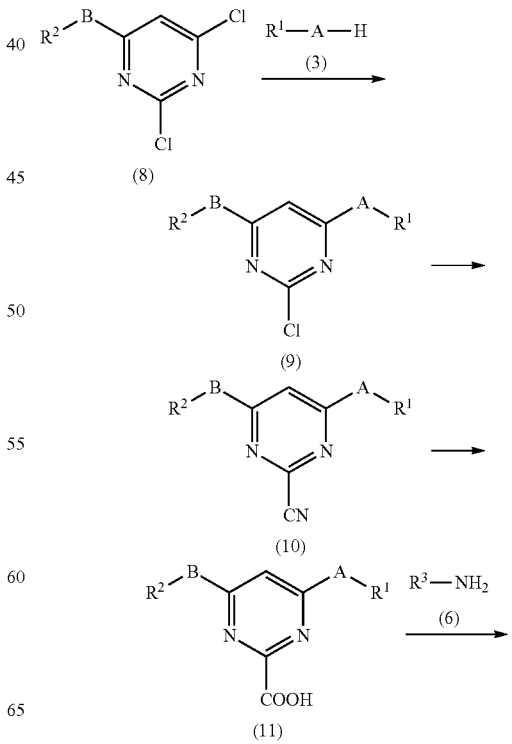

-continued

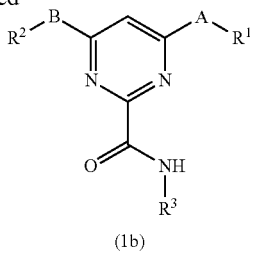

(1b)

wherein A, B, $R^1$, $R^2$, and $R^3$ are as defined above.

A compound of the formula (8) is reacted with $R^1$-A-H (3) to obtain a compound of the formula (9), which is cyanated to obtain a compound (10), followed by hydrolysis to obtain a compound of the formula (11). The compound of the formula (11) is reacted with amine ($R^3$—$NH_2$) to obtain a compound of the formula (1b).

The reaction of the compound (8) with the compound (3) is preferably carried out by reacting the compound (8) with a base and then with the compound (3), as in the first step. The base is preferably an alkali metal alkoxide or the like. The reaction can be carried out at room temperature to reflux temperature for 1 to 48 hours in an ether solvent such as tetrahydrofuran.

The cyanation reaction of the compound (9) is carried out, for example, by reacting the compound (9) with a cyanating agent such as zinc dicyanide in the presence of tetrakis (triphenylphosphine)palladium or the like. The reaction can be carried out at room temperature to reflux temperature in an amide solvent such as dimethylformamide or dimethylacetamide.

The hydrolysis of the compound (10) can be carried out in the presence of a base such as sodium hydroxide or potassium hydroxide.

The reaction of the compound (11) with $R^3$—$NH_2$ (6) can be carried out in the same way as in the third step. Specifically, the reaction is preferably carried out in the presence of, for example, a benzotriazole such as 1-hydroxybenzotriazole (HOBt), N-hydroxysuccinimide (HOSu), 1-hydroxybenzotriazole (HOAt), HBTU, or HATU and a condensing agent such as 1-ethyl-3-(3-dimethylaminopropyl)carbodiimide (EDC) or dicyclohexylcarbodiimide.

The amide compound of the present invention or a salt thereof has excellent Aβ aggregation inhibitory activity, as shown in Examples mentioned later, and is useful as an Aβ aggregation inhibitor and as a prophylactic or therapeutic agent for diseases involving amyloid deposition or Aβ aggregation in animals including humans, for example, Alzheimer's disease and Down syndrome.

The dose of the amide compound of the present invention or a salt thereof used as a pharmaceutical for human bodies is in the range of 1 mg to 1 g, preferably 10 mg to 300 mg, per day for an adult.

A pharmaceutical composition containing the amide compound of the present invention or a salt thereof can be prepared according to any of various formulation methods by selecting a preparation appropriate for an administration method and using a pharmaceutically acceptable carrier. Examples of the dosage form of the pharmaceutical composition containing the amide compound of the present invention or a salt thereof as a principal ingredient can include oral preparations such as tablets, powders, granules, capsules, solutions, syrups, elixirs, and oily or aqueous suspensions.

A stabilizer, an antiseptic, and a solubilizer may be used in the preparation as an injection. A solution optionally containing these auxiliary agents may be placed in a container and then freeze-dried, for example, to obtain a solid preparation to be prepared before use. Also, a single dose may be placed in one container, or multiple doses may be placed in one container.

Examples of preparations for external use can include solutions, suspensions, emulsions, ointments, gels, creams, lotions, sprays, and patches.

The solid preparation contains pharmaceutically acceptable additives in addition to the amide compound of the present invention or a salt thereof and can be formulated by mixing the amide compound or a salt thereof with the additives selected according to the need from, for example, fillers, expanders, binders, disintegrants, dissolution promoters, wetting agents, and lubricants.

Examples of liquid preparations can include solutions, suspensions, and emulsions. These liquid preparations may contain an additive such as a suspending agent or an emulsifying agent.

EXAMPLES

Hereinafter, the present invention will be specifically described with reference to Examples. However, the scope of the present invention is not intended to be limited by Examples below.

Synthesis Example 1

1) Synthesis of 2-bromo-6-phenoxypyridine

To an eggplant-shaped flask, 2.64 g (55 mmol) of sodium hydride having a content of 50% and 75 mL of dimethylformamide were added, and the mixture was stirred. The reaction vessel was cooled to 0° C., and 4.7 g (50 mmol) of phenol dissolved in 25 mL of dimethylformamide was gradually added dropwise thereto. To this reaction vessel, 11.9 g (50 mmol) of 2,6-dibromopyridine was added, and the mixture was heated to 60 to 65° C. and stirred for 18 hours. Subsequently, the reaction mixture was separated into aqueous and organic layers by the addition of water and ethyl acetate, and the recovered organic layer was washed with a 1 M aqueous sodium hydroxide solution and saturated saline, dehydrated over sodium sulfate, and then filtered through a cotton plug. The solvent in the filtrate was distilled off under reduced pressure, and crystals deposited by the addition of hexane were washed by the slurry method and then dried to obtain the compound of interest as a white solid (9.1 g, yield: 72%).

$^1$H-NMR (400 MHz, $CDCl_3$, rt): δ 6.68 (1H, d, J=8.6 Hz), 7.07 (2H, d, J=8.6 Hz), 7.12 (1H, d, J=8.6 Hz), 7.14 (1H, t, J=8.6 Hz), 7.33 (2H, t, J=8.6 Hz), 7.43 (1H, t, J=8.6 Hz) ppm ESI MS (positive): [M+Na]$^+$ Found m/z 272

2) 6-Phenoxy-N-isoamylpicolinamide

To an eggplant-shaped flask, 9.1 g (36 mmol) of 2-bromo-6-phenoxypyridine and 300 mL of diethyl ether were added, and the mixture was stirred. The reaction vessel was cooled to −78° C. 15.2 mL (40 mmol) of a 2.6 M solution of n-BuLi in hexane was added thereto, and the mixture was stirred for 15 minutes. The temperature of the reaction vessel was raised to room temperature, and the reaction mixture was further stirred for 1 hour while carbon dioxide was blown into the reaction vessel. Subsequently, water, ethyl acetate, and a 1 M aqueous sodium hydroxide solution were added thereto. After confirmation that pH was 14, the reaction mixture was separated into aqueous and organic layers, and the aqueous layer was recovered. To the recovered aqueous layer, 1 M hydrochloric acid was added until pH 1, and then ethyl acetate was added for separation into aqueous and organic layers. The organic layer was recovered, washed with saturated saline, dehydrated over sodium sulfate, and then filtered through a cotton plug, and the solvent in the filtrate was distilled off under reduced pressure to obtain 2.7 g of a liquid (6-phenoxy-picolinic acid, approximately 12.5 mmol). This liquid in an unpurified form was transferred to an eggplant-shaped flask. 125 mL of dimethylformamide was added thereto, and the mixture was stirred. To this mixture, 2.9 mL (25 mmol) of isoamylamine, 6.5 mL (37.5 mmol) of N,N-diisopropylethylamine, 3.8 g (25 mmol) of 1-hydroxybenzotriazole (HOBt), and 4.8 g (25 mmol) of 1-ethyl-3-(3-dimethylaminopropyl)carbodiimide (EDC) were added in this order, and the resulting mixture was stirred overnight with the temperature kept at room temperature. Subsequently, the reaction mixture was separated into aqueous and organic layers by the addition of water and ethyl acetate, and the recovered organic layer was washed with saturated saline, dehydrated over sodium sulfate, and then filtered through a cotton plug. The solvent in the filtrate was distilled off under reduced pressure, and the obtained residue was purified by silica gel column chromatography to obtain the compound of interest as a colorless oil (2.1 g, yield: 20%).

$^1$H-NMR (400 MHz, CDCl$_3$, rt): δ 0.78 (6H, d, J=6.8 Hz), 1.28 (2H, dt, J=6.8 Hz, 6.8 Hz), 1.42 (1H, m), 3.27 (2H, dt, J=6.8 Hz, 6.8 Hz), 6.90 (1H, d, J=8.6 Hz), 7.04 (2H, d, J=8.6 Hz), 7.13 (1H, t, J=8.6 Hz), 7.31 (2H, t, J=8.6 Hz), 7.45 (1H, br), 7.71 (1H, t, J=8.6 Hz), 7.79 (1H, d, J=8.6 Hz) ppm ESI MS (positive): [M+Na]$^+$ Found m/z 307

3) 4-Benzyl-6-phenoxy-N-isoamylpicolinamide (Compound 1)

To a test tube, 39 mg (137 μmol) of 6-phenoxy-N-isoamylpicolinamide was added, then 1 mL of tetrahydrofuran was added, and the mixture was stirred. The reaction vessel was cooled to 0° C. 137 μL (137 μmol) of a 1.0 M solution of t-BuMgCl in tetrahydrofuran was added thereto, and the mixture was stirred for 30 minutes. Subsequently, 36 μL (288 μmol) of BF$_3$.OEt$_2$ was added thereto, and the mixture was stirred for 15 minutes. The reaction vessel was cooled to −30° C. 550 μL (274 μmol) of a 0.5 M solution of BnMgCl.LiCl in tetrahydrofuran was added thereto, and the mixture was stirred for 2 hours. After raising of the temperature to room temperature, 67 mg (274 μmol) of chloranil was added thereto, and the mixture was stirred for 6 hours. The reaction mixture was quenched by the addition of 1 mL of a saturated aqueous solution of ammonia and then separated into aqueous and organic layers by the addition of water and ethyl acetate. The recovered organic layer was washed with saturated saline, dehydrated over sodium sulfate, and then filtered through a cotton plug. The solvent in the filtrate was distilled off under reduced pressure. The obtained residue was purified by preparative TLC, and the recovered compound of interest was further purified by preparative HPLC to obtain compound 1 as a colorless oil (9.1 mg, yield: 17%).

$^1$H-NMR (500 MHz, CDCl$_3$, rt): δ 0.81 (6H, d, J=6.8 Hz), 1.29 (2H, dt, J=6.8 Hz, 6.8 Hz), 1.43 (1H, m), 3.27 (2H, dt, J=6.8 Hz, 6.8 Hz), 3.93 (2H, s), 6.75 (1H, s), 7.05 (2H, d, J=8.0 Hz), 7.12 (2H, d, J=8.0 Hz), 7.17 (2H, t, J=8.0 Hz), 7.24 (2H, d, J=8.0 Hz), 7.33 (2H, t, J=8.0 Hz), 7.42 (1H, br), 7.70 (1H, s) ppm $^{13}$C-NMR (125 MHz, CDCl$_3$, rt): δ 22.3, 25.5, 37.4, 38.0, 41.4, 113.8, 117.7, 121.3, 124.8, 126.8, 128.8, 129.0, 129.5, 138.2, 153.7, 162.5, 163.6 ppm ESI MS (positive): [M+Na]$^+$ Found m/z 397

Synthesis Example 2

4-(Naphthalen-2-yl)methyl-6-phenoxy-N-isoamylpicolinamide (Compound 2)

To a test tube, 28 mg (100 μmol) of 6-phenoxy-N-isoamylpicolinamide was added, then 1 mL of tetrahydrofuran was added, and the mixture was stirred. The reaction vessel was cooled to 0° C. 100 μL (100 μmol) of a 1.0 M solution of t-BuMgCl in tetrahydrofuran was added thereto, and the mixture was stirred for 30 minutes. Subsequently, 26 μL (210 μmol) of BF$_3$.OEt$_2$ was added thereto, and the mixture was stirred for 15 minutes. The reaction vessel was cooled to −30° C. 800 μL (200 μmol) of a 0.25 M solution of a (naphthalen-2-yl)methyl magnesium chloride-lithium chloride complex in tetrahydrofuran was added thereto, and the mixture was stirred for 1 hour. After raising of the temperature to room temperature, 49 mg (200 μmol) of chloranil was added thereto, and the mixture was stirred overnight. The reaction mixture was quenched by the addition of 1 mL of a saturated aqueous solution of ammonia and then separated into aqueous and organic layers by the addition of water and ethyl acetate. The recovered organic layer was washed with saturated saline, dehydrated over sodium sulfate, and then filtered through a cotton plug. The solvent in the filtrate was distilled off under reduced pressure. The obtained residue was purified by preparative TLC, and the recovered compound of interest was further purified by preparative HPLC to obtain the compound of interest as a colorless oil (6.0 mg, yield: 14%).

$^1$H-NMR (500 MHz, CDCl$_3$, rt): δ 0.79 (6H, d, J=6.3 Hz), 1.28 (2H, dt, J=6.3 Hz), 1.43 (1H, m), 3.26 (2H, dt, J=6.8 Hz, 6.8 Hz), 4.09 (2H, s), 6.79 (1H, s), 7.04 (2H, d, J=7.4 Hz), 7.14 (1H, t, J=7.4 Hz), 7.22 (1H, d, J=7.4 Hz), 7.31 (2H, t, J=7.4 Hz), 7.39 (3H, m), 7.59 (1H, br), 7.72 (4H, m) ppm ESI MS (positive): [M+Na]$^+$ Found m/z 473

Synthesis Example 3

1) 6-Phenoxy-N-(4-methylpentyl)picolinamide

To an eggplant-shaped flask, 4.7 g (19 mmol) of 2-bromo-6-phenoxypyridine and 50 mL of diethyl ether were added, and the mixture was stirred. The reaction vessel was cooled to −78° C. 22.4 mL (13.6 mmol) of a 1.65 M solution of n-BuLi in hexane was added thereto, and the mixture was stirred for 15 minutes. The temperature of the reaction vessel was raised to room temperature, and the reaction mixture was further stirred for 1 hour while carbon dioxide was blown into the reaction vessel. Subsequently, water, ethyl acetate, and a 1 M aqueous sodium hydroxide solution were added thereto. After confirmation that pH was 14, the reaction mixture was separated into aqueous and organic layers, and the aqueous layer was recovered. To the recovered aqueous layer, 1 M hydrochloric acid was added until pH 1, and then ethyl acetate was added for separation into aqueous and organic layers. The organic layer was recovered, washed with saturated saline, dehydrated over sodium sulfate, and then filtered through a cotton plug, and the solvent in the filtrate was distilled off under reduced pressure to obtain 1 g of a liquid (6-phenoxypicolinic acid, approximately 4.7 mmol). This liquid in an unpurified form was transferred to an eggplant-shaped flask. 30 mL of dimethylformamide was added thereto, and the mixture was stirred. To this mixture, 1.2 mL (10 mmol) of 4-methylpentylamine, 1.6 mL (9.4 mmol) of N,N-diisopropylethylamine, and 2.1 g (5.6 mmol) of HATU were added in this order, and the resulting mixture was stirred overnight with the temperature kept at room temperature. Subsequently, the reaction mixture was separated into aqueous and organic layers by the addition of water and ethyl acetate, and the recovered organic layer was washed with saturated saline, dehydrated over sodium sulfate, and then filtered through a cotton plug. The solvent in the filtrate was distilled off under reduced pressure, and the obtained residue was purified by silica gel column chromatography to obtain the compound of interest as a colorless oil (822 mg, yield: 15%).

$^1$H-NMR (500 MHz, CDCl$_3$, rt): δ 0.87 (6H, d, J=6.8 Hz), 1.15 (2H, dt, J=6.8 Hz, 6.8 Hz), 1.51 (1H, m), 3.34 (2H, dt, J=6.8 Hz, 6.8 Hz), 7.02 (1H, d, J=8.0 Hz), 7.16 (2H, d, J=8.0 Hz), 7.25 (1H, t, J=8.0 Hz), 7.43 (2H, t, J=8.0 Hz), 7.56 (1H, br), 7.83 (1H, t, J=8.0 Hz), 7.90 (1H, d, J=8.0 Hz) ppm ESI MS (positive): [M+Na]$^+$ Found m/z 321

2) 4-Benzyl-6-phenoxy-N-(4-methylpentyl)picolinamide (Compound 3)

To a test tube, 30 mg (100 μmol) of 6-phenoxy-N-(4-methylpentyl)picolinamide was added, then 1 mL of tetrahydrofuran was added, and the mixture was stirred. The reaction vessel was cooled to 0° C. 100 μL (100 μmol) of a 1.0 M solution of t-BuMgCl in tetrahydrofuran was added thereto, and the mixture was stirred for 30 minutes. Subsequently, 26 μL (210 μmol) of BF$_3$.OEt$_2$ was added thereto, and the mixture was stirred for 15 minutes. The reaction vessel was cooled to −30° C. 400 μL (200 μmol) of a 0.5 M solution of BnMgCl.LiCl in tetrahydrofuran was added thereto, and the mixture was stirred for 2 hours. After raising of the temperature to room temperature, 49 mg (200 μmol) of chloranil was added thereto, and the mixture was stirred overnight. The reaction mixture was quenched by the addition of 1 mL of a saturated aqueous solution of ammonia and then separated into aqueous and organic layers by the addition of water and ethyl acetate. The recovered organic layer was washed with saturated saline, dehydrated over sodium sulfate, and then filtered through a cotton plug. The solvent in the filtrate was distilled off under reduced pressure. The obtained residue was purified by preparative TLC, and the recovered compound of interest was further purified by preparative HPLC to obtain compound 3 as a colorless oil (4.0 mg, yield: 10%).

$^1$H-NMR (500 MHz, CDCl$_3$, rt): δ 0.86 (6H, d, J=6.3 Hz), 1.13 (2H, m), 1.50 (3H, m), 3.31 (2H, dt, J=6.8 Hz, 6.8 Hz), 4.02 (2H, s), 6.83 (1H, s), 7.13 (2H, d, J=7.4 Hz), 7.18-7.28 (4H, m), 7.32 (2H, t, J=7.4 Hz), 7.41 (2H, t, J=7.4 Hz), 7.52 (1H, br), 7.79 (1H, s) ppm $^{13}$C-NMR (125 MHz, CDCl$_3$, rt): δ 22.5, 27.2, 27.7, 35.9, 39.5, 41.4, 113.8, 117.8, 121.2, 124.9, 126.8, 128.8, 129.0, 129.5, 138.3, 147.8, 153.7, 155.7, 162.5, 163.7 ppm ESI MS (positive): [M+Na]$^+$ Found m/z 411

Synthesis Example 4

1) 2-Bromo-6-cyclohexyloxypyridine

To an eggplant-shaped flask, 528 mg (11 mmol) of sodium hydride having a content of 50% and 10 mL of dimethylformamide were added, and the mixture was stirred. The reaction vessel was cooled to 0° C., and 1.05 mL (1.0 mmol) of cyclohexyl alcohol dissolved in 10 mL of dimethylformamide was gradually added dropwise thereto. To this reaction vessel, 2.37 g (10 mmol) of 2,6-dibromopyridine was added, and the mixture was heated to 90° C. and stirred for 18 hours. Subsequently, the reaction mixture was separated into aqueous and organic layers by the addition of water and ethyl acetate, and the recovered organic layer was washed with a 1 M aqueous sodium hydroxide solution and saturated saline, dehydrated over sodium sulfate, and then filtered through a cotton plug. The solvent in the filtrate was distilled off under reduced pressure, and the residue was purified by silica gel column chromatography to obtain the compound of interest as a white solid (1.63 g, yield: 64%).

$^1$H-NMR (500 MHz, CDCl$_3$, rt): δ 1.25-1.63 (6H, m), 1.78 (2H, m), 1.99 (2H, m), 5.02 (1H, m), 6.63 (1H, d, J=8.6 Hz), 7.00 (2H, d, J=8.6 Hz), 7.39 (1H, t, J=8.6 Hz) ppm ESI MS (positive): [M+Na]$^+$ Found m/z 278

2) 6-Cyclohexyloxy-N-isoamylpicolinamide

To an eggplant-shaped flask, 1.63 g (6.4 mmol) of 2-bromo-6-cyclohexyloxypyridine and 64 mL of diethyl ether were added, and the mixture was stirred. The reaction vessel was cooled to −78° C., and 6.2 mL (7.0 mmol) of a 1.14 M solution of n-BuLi in hexane was added thereto, and the mixture was stirred for 15 minutes. The temperature of the reaction vessel was raised to room temperature, and the reaction mixture was further stirred for 1 hour while carbon dioxide was blown into the reaction vessel. Subsequently, water, ethyl acetate, and a 1 M aqueous sodium hydroxide solution were added thereto. After confirmation that pH was 14, the reaction mixture was separated into aqueous and organic layers, and the aqueous layer was recovered. To the recovered aqueous layer, 1 M hydrochloric acid was added until pH 1, and then ethyl acetate was added for separation into aqueous and organic layers. The organic layer was recovered, washed with saturated saline, dehydrated over sodium sulfate, and then filtered through a cotton plug, and the solvent in the filtrate was distilled off under reduced pressure to obtain 370 mg of a liquid (6-cyclohexyloxypicolinic acid, approximately 1.67 mmol). This liquid in an unpurified form was transferred to an eggplant-shaped flask. 17 mL of dimethylformamide was added thereto, and the mixture was stirred. To this mixture, 390 μL (3.34 mmol) of isoamylamine, 870 μL (5.01 mmol) of N,N-diisopropylethylamine, 511 mg (3.34 mmol) of HOBt, and 640 mg (3.34 mmol) of EDC were added in this order, and the resulting mixture was stirred overnight with the temperature kept at room temperature. Subsequently, the reaction mixture was separated into aqueous and organic layers by the addition of water and ethyl acetate, and the recovered organic layer was washed with saturated saline, dehydrated over sodium sulfate, and then filtered through a cotton plug. The solvent in the filtrate was distilled off under reduced pressure, and the obtained residue was purified by silica gel column chromatography to obtain the compound of interest as a colorless oil (265 mg, yield: 14%).

$^1$H-NMR (400 MHz, CDCl$_3$, rt): δ 0.98 (6H, d, J=6.8 Hz), 1.25-1.74 (9H, m), 1.82 (2H, m), 2.04 (2H, m), 3.49 (2H, dt, J=6.8 Hz, 6.8 Hz), 4.96 (1H, m), 6.83 (1H, d, J=8.0 Hz), 7.69 (1H, t, J=8.0 Hz), 7.75 (1H, d, J=8.0 Hz) ppm ESI MS (positive): [M+Na]$^+$ Found m/z 313

3) 4-Benzyl-6-cyclohexyloxy-N-isoamylpicolinamide (Compound 4)

To a test tube, 29 mg (100 μmol) of 6-cyclohexyloxy-N-isoamylpicolinamide was added, then 1 mL of tetrahydrofuran was added, and the mixture was stirred. The reaction vessel was cooled to 0° C. 100 μL (100 μmol) of a 1.0 M solution of t-BuMgCl in tetrahydrofuran was added thereto, and the mixture was stirred for 30 minutes. Subsequently, 26 μL (210 μmol) of $BF_3.OEt_2$ was added thereto, and the mixture was stirred for 15 minutes. The reaction vessel was cooled to −30° C. 800 μL (200 μmol) of a 0.25 M solution of BnMgCl.LiCl in tetrahydrofuran was added thereto, and the mixture was stirred for 1 hour. After raising of the temperature to room temperature, 49 mg (200 μmol) of chloranil was added thereto, and the mixture was stirred overnight. The reaction mixture was quenched by the addition of 1 mL of a saturated aqueous solution of ammonia and then separated into aqueous and organic layers by the addition of water and ethyl acetate. The recovered organic layer was washed with saturated saline, dehydrated over sodium sulfate, and then filtered through a cotton plug. The solvent in the filtrate was distilled off under reduced pressure. The obtained residue was purified by preparative TLC, and the recovered compound of interest was further purified by preparative HPLC to obtain compound 4 as a colorless oil (6.0 mg, yield: 14%).

$^1$H-NMR (500 MHz, $CDCl_3$, rt): δ 0.97 (6H, d, J=6.8 Hz), 1.25-1.74 (9H, m), 1.82 (2H, m), 2.22 (2H, m), 3.47 (2H, dt, J=6.8 Hz, 6.8 Hz), 3.95 (2H, s), 4.93 (1H, m) 6.62 (1H, s), 7.19 (2H, d, J=8.0 Hz), 7.23 (1H, t, J=8.0 Hz), 7.30 (2H, t, J=8.0 Hz), 7.64 (1H, s) 7.74 (1H, br) ppm ESI MS (positive): [M+Na]$^+$ Found m/z 403

Synthesis Example 5

1) 2-Bromo-6-benzyloxypyridine

To an eggplant-shaped flask, 528 mg (11 mmol) of sodium hydride having a content of 50% and 5 mL of dimethylformamide were added, and the mixture was stirred. The reaction vessel was cooled to 0° C., and 1.73 mL (10.0 mmol) of benzyl alcohol dissolved in 5 mL of dimethylformamide was gradually added dropwise thereto. To this reaction vessel, 2.37 g (10 mmol) of 2,6-dibromopyridine was added, and the mixture was heated to 100° C. and stirred for 18 hours. Subsequently, the reaction mixture was separated into aqueous and organic layers by the addition of water and ethyl acetate, and the recovered organic layer was washed with a 1 M aqueous sodium hydroxide solution and saturated saline, dehydrated over sodium sulfate, and then filtered through a cotton plug. The solvent in the filtrate was distilled off under reduced pressure, and the residue was purified by silica gel column chromatography to obtain the compound of interest as a colorless oil (2.08 g, yield: 79%).

$^1$H-NMR (500 MHz, $CDCl_3$, rt): δ 5.37 (2H, s), 6.75 (1H, d, J=8.0 Hz), 7.09 (1H, d, J=8.0 Hz), 7.32-7.49 (6H, m) ppm ESI MS (positive): [M+Na]$^+$ Found m/z 286

2) 6-Benzyloxy-N-isoamylpicolinamide

To an eggplant-shaped flask, 2.08 g (7.9 mmol) of 2-bromo-6-benzyloxypyridine and 79 mL of diethyl ether were added, and the mixture was stirred. The reaction vessel was cooled to −78° C. 5.3 mL (8.7 mmol) of a 1.65 M solution of n-BuLi in hexane was added thereto, and the mixture was stirred for 15 minutes. The temperature of the reaction vessel was raised to room temperature, and the reaction mixture was further stirred for 1 hour while carbon dioxide was blown into the reaction vessel. Subsequently, water, ethyl acetate, and a 1 M aqueous sodium hydroxide solution were added thereto. After confirmation that pH was 14, the reaction mixture was separated into aqueous and organic layers, and the aqueous layer was recovered. To the recovered aqueous layer, 1 M hydrochloric acid was added until pH 1, and then ethyl acetate was added for separation into aqueous and organic layers. The organic layer was recovered, washed with saturated saline, dehydrated over sodium sulfate, and then filtered through a cotton plug, and the solvent in the filtrate was distilled off under reduced pressure to obtain 547 mg of a liquid (6-benzyloxypicolinic acid, approximately 2.39 mmol). This liquid in an unpurified form was transferred to an eggplant-shaped flask. 24 mL of dimethylformamide was added thereto, and the mixture was stirred. To this mixture, 560 μL (4.78 mmol) of isoamylamine, 830 μL (4.78 mmol) of N,N-diisopropylethylamine, 37 mg (239 μmol) of HOBt, and 549 mg (2.87 mmol) of EDC were added in this order, and the resulting mixture was stirred overnight with the temperature kept at room temperature. Subsequently, the reaction mixture was separated into aqueous and organic layers by the addition of water and ethyl acetate, and the recovered organic layer was washed with saturated saline, dehydrated over sodium sulfate, and then filtered through a cotton plug. The solvent in the filtrate was distilled off under reduced pressure, and the obtained residue was purified by silica gel column chromatography to obtain the compound of interest as a colorless oil (34.4 mg, yield: 1.4%).

$^1$H-NMR (500 MHz, $CDCl_3$, rt): δ 0.88 (6H, d, J=6.8 Hz), 1.42 (2H, dt, J=6.8 Hz, 6.8 Hz), 1.59 (1H, m), 3.38 (2H, dt, J=6.8 Hz, 6.8 Hz), 5.30 (2H, s), 6.86 (1H, d, J=8.0 Hz), 7.25 (1H, t, J=8.0 Hz), 7.30 (2H, t, J=8.0 Hz), 7.36 (2H, d, J=8.0 Hz), 7.58 (1H, br), 7.64 (1H, t, J=8.0 Hz), 7.71 (1H, d, J=8.0 Hz) ppm ESI MS (positive): [M+Na]$^+$ Found m/z 321

3) 6-Benzyloxy-4-benzyl-N-isoamylpicolinamide (Compound 5)

To a test tube, 30 mg (100 μmol) of 6-benzyloxy-N-isoamylpicolinamide was added, then 1 mL of tetrahydrofuran was added, and the mixture was stirred. The reaction vessel was cooled to 0° C. 100 μL (100 μmol) of a 1.0 M solution of t-BuMgCl in tetrahydrofuran was added thereto, and the mixture was stirred for 30 minutes. Subsequently, 26 μL (210 μmol) of $BF_3.OEt_2$ was added thereto, and the mixture was stirred for 15 minutes. The reaction vessel was cooled to −30° C. 800 μL (200 μmol) of a 0.25 M solution of BnMgCl.LiCl in tetrahydrofuran was added thereto, and the mixture was stirred for 1 hour. After raising of the temperature to room temperature, 49 mg (200 μmol) of chloranil was added thereto, and the mixture was stirred overnight. The reaction mixture was quenched by the addition of 1 mL of a saturated aqueous solution of ammonia and then separated into aqueous and organic layers by the addition of water and ethyl acetate. The recovered organic layer was washed with saturated saline, dehydrated over sodium sulfate, and then filtered through a cotton plug. The solvent in the filtrate was distilled off under reduced pressure. The obtained residue was purified by preparative TLC, and the recovered compound of interest was further purified by preparative HPLC to obtain compound 5 as a colorless oil (3.0 mg, yield: 7.7%).

¹H-NMR (500 MHz, CDCl₃, rt): δ 0.96 (6H, d, J=6.8 Hz), 1.50 (2H, dt, J=6.8 Hz, 6.8 Hz), 1.67 (1H, m), 3.45 (2H, dt, J=6.8 Hz, 6.8 Hz), 3.97 (2H, s), 5.35 (2H, s), 6.73 (1H, s), 7.19 (2H, d, J=8.0 Hz), 7.23 (1H, t, J=8.0 Hz), 7.28-7.35 (3H, m), 7.38 (2H, t, J=8.0 Hz), 7.43 (2H, d, J=8.0 Hz), 7.65 (1H, br), 7.70 (1H, s) ppm ESI MS (positive): [M+Na]⁺ Found m/z 411

Synthesis Example 6

1) 2-Bromo-6-(3-methylbutoxy)pyridine

To an eggplant-shaped flask, 528 mg (11 mmol) of sodium hydride having a content of 50% and 5 mL of dimethylformamide were added, and the mixture was stirred. The reaction vessel was cooled to 0° C., and 1.08 mL (10.0 mmol) of 3-methylbutanol dissolved in 5 mL of dimethylformamide was gradually added dropwise thereto. To this reaction vessel, 2.37 g (10 mmol) of 2,6-dibromopyridine was added, and the mixture was heated to 100° C. and stirred for 18 hours. Subsequently, the reaction mixture was separated into aqueous and organic layers by the addition of water and ethyl acetate, and the recovered organic layer was washed with a 1 M aqueous sodium hydroxide solution and saturated saline, dehydrated over sodium sulfate, and then filtered through a cotton plug. The solvent in the filtrate was distilled off under reduced pressure, and the residue was purified by silica gel column chromatography to obtain the compound of interest as a colorless oil (2.35 g, yield: 96%).

¹H-NMR (400 MHz, CDCl₃, rt): δ 0.97 (6H, d, J=6.8 Hz), 1.65 (2H, m), 1.81 (1H, m), 4.31 (2H, m), 6.67 (1H, d, J=8.0 Hz), 7.04 (1H, d, J=8.0 Hz), 7.40 (1H, t, J=8.0 Hz) ppm ESI MS (positive): [M+Na]⁺ Found m/z 266

2) 6-(3-Methylbutoxy)-N-phenylethylpicolinamide

To an eggplant-shaped flask, 565 mg (2.3 mmol) of 2-bromo-6-(3-methylbutoxy)pyridine and 13 mL of diethyl ether were added, and the mixture was stirred. The reaction vessel was cooled to −78° C. 3.17 mL (2.5 mmol) of a 0.8 M solution of n-BuLi in hexane was added thereto, and the mixture was stirred for 15 minutes. The temperature of the reaction vessel was raised to room temperature, and the reaction mixture was further stirred for 1 hour while carbon dioxide was blown into the reaction vessel. Subsequently, water, ethyl acetate, and a 1 M aqueous sodium hydroxide solution were added thereto. After confirmation that pH was 14, the reaction mixture was separated into aqueous and organic layers, and the aqueous layer was recovered. To the recovered aqueous layer, 1 M hydrochloric acid was added until pH 1, and then ethyl acetate was added for separation into aqueous and organic layers. The organic layer was recovered, washed with saturated saline, dehydrated over sodium sulfate, and then filtered through a cotton plug, and the solvent in the filtrate was distilled off under reduced pressure to obtain 140 mg of a liquid (6-(3-methylbutoxy) picolinic acid, approximately 0.67 mmol). This liquid in an unpurified form was transferred to an eggplant-shaped flask. 7 mL of dimethylformamide was added thereto, and the mixture was stirred. To this mixture, 169 μL (1.34 mmol) of phenylethylamine, 350 μL (2.01 mmol) of N,N-diisopropylethylamine, 205 mg (1.34 mmol) of HOBt, and 257 mg (1.34 mmol) of EDC were added in this order, and the resulting mixture was stirred overnight with the temperature kept at room temperature. Subsequently, the reaction mixture was separated into aqueous and organic layers by the addition of water and ethyl acetate, and the recovered organic layer was washed with saturated saline, dehydrated over sodium sulfate, and then filtered through a cotton plug. The solvent in the filtrate was distilled off under reduced pressure, and the obtained residue was purified by silica gel column chromatography to obtain the compound of interest as a colorless oil (63.7 mg, yield: 9%).

¹H-NMR (400 MHz, CDCl₃, rt): δ 0.96 (6H, d, J=6.8 Hz), 1.63 (2H, dt, J=6.8 Hz, 6.8 Hz), 1.79 (1H, m), 2.93 (2H, t, J=6.8 Hz), 3.73 (2H, dt, J=6.8 Hz, 6.8 Hz), 4.17 (2H, t, J=6.8 Hz), 6.83 (1H, s), 7.21-7.34 (5H, m), 7.67 (1H, t, J=8.0 Hz), 7.76 (1H, d, J=8.0 Hz), 7.86 (1H, br) ppm ESI MS (positive): [M+Na]⁺ Found m/z 335

3) 4-Benzyl-6-(3-methylbutoxy)-N-phenylethylpicolinamide (Compound 6)

To a test tube, 31 mg (100 μmol) of 6-(3-methylbutoxy)-N-phenylethylpicolinamide was added, then 1 mL of tetrahydrofuran was added, and the mixture was stirred. The reaction vessel was cooled to 0° C. 100 μL (100 μmol) of a 1.0 M solution of t-BuMgCl in tetrahydrofuran was added thereto, and the mixture was stirred for 30 minutes. Subsequently, 26 μL (210 μmol) of BF₃.OEt₂ was added thereto, and the mixture was stirred for 15 minutes. The reaction vessel was cooled to −30° C. 400 μL (200 μmol) of a 0.5 M solution of BnMgCl.LiCl in tetrahydrofuran was added thereto, and the mixture was stirred for 1 hour. After raising of the temperature to room temperature, 49 mg (200 μmol) of chloranil was added thereto, and the mixture was stirred overnight. The reaction mixture was quenched by the addition of 1 mL of a saturated aqueous solution of ammonia and then separated into aqueous and organic layers by the addition of water and ethyl acetate. The recovered organic layer was washed with saturated saline, dehydrated over sodium sulfate, and then filtered through a cotton plug. The solvent in the filtrate was distilled off under reduced pressure. The obtained residue was purified by preparative TLC, and the recovered compound of interest was further purified by preparative HPLC to obtain compound 6 as a colorless oil (2.0 mg, yield: 5.0%).

¹H-NMR (500 MHz, CDCl₃, rt): δ 0.95 (6H, d, J=6.8 Hz), 1.60 (2H, m), 1.77 (1H, m), 2.92 (2H, t, J=6.8 Hz), 3.73 (2H, dt, J=6.8 Hz), 3.95 (2H, s), 4.14 (2H, t, J=6.8 Hz), 6.63 (1H, s), 7.19 (2H, d, J=8.0 Hz), 7.21-7.35 (8H, m), 7.66 (1H, s), 7.84 (1H, br) ppm ESI MS (positive): [M+Na]⁺ Found m/z 425

Synthesis Examples 7 to 11

The following compounds were synthesized in the same way as in Synthesis Examples 1 to 6:
4-Benzyl-6-(naphthalen-1-yl)methyloxy-N-isoamylpicolinamide (compound 7)
4-Benzyl-6-(4-methoxyphenyloxy)-N-isoamylpicolinamide (compound 8)
4-Benzyl-6-(4-hydroxyphenyloxy)-N-isoamylpicolinamide (compound 9)
4-(4'-Biphenylmethyl)-6-phenoxy-N-isoamylpicolinamide (compound 10)
4-(Naphthalen-1-yl)methyl-6-phenoxy-N-isoamylpicolinamide (compound 11)

Synthesis Example 12

(1) 4-Benzyl-2-chloro-6-phenoxypyrimidine

To a solution of potassium tert-butoxide (621 mg, 5.53 mmol) dissolved in tetrahydrofuran (16 mL), phenol (501 mg, 5.53 mmol) was added at 0° C. in an argon atmosphere. The mixture was stirred at room temperature for 5 minutes, and a solution containing 4-benzyl-2,6-dichloropyrimidine (WO2004-099192) (1.23 g, 5.27 mmol) in tetrahydrofuran (10 mL) was then gradually added dropwise thereto at 0° C.

The mixture was stirred at room temperature for 3 hours, and the reaction was then terminated by the addition of a saturated aqueous solution of ammonium chloride. The product was subjected to extraction with ethyl acetate (×3). The organic layer was washed with saline, dried over sodium sulfate, and then concentrated. The residue was purified by flash column chromatography (hexane/AcOEt=99/1 to 90/10) to obtain 4-benzyl-2-chloro-6-phenoxypyrimidine (yield: 1.20 g, 79%).

$^1$H NMR (500 MHz, CDCl$_3$) δ: 4.03 (s, 2H), 6.48 (s, 1H), 7.07 (d, J=8.0 Hz, 2H), 7.20-7.43 (m, 8H).

(2) 4-Benzyl-6-phenoxypyrimidine-2-carbonitrile

To a solution of 4-benzyl-2-chloro-6-phenoxypyridine (446 mg, 1.55 mmol) dissolved in DMF (7.8 mL), zinc dicyanide (273 mg, 2.33 mmol) and tetrakis(triphenylphosphine)palladium(0) (89.6 mg, 0.0775 mmol) were added at room temperature in an argon atmosphere. The mixture was stirred at 160° C. for 1 hour, and the reaction was then terminated by the addition of a 2 M aqueous sodium hydroxide solution. The product was subjected to extraction with ethyl acetate (×3). The organic layer was washed with saline, dried over sodium sulfate, and then concentrated. The residue was purified by flash column chromatography (hexane/AcOEt=99/1 to 90/10) to obtain 4-benzyl-6-phenoxypyrimidine-2-carbonitrile (yield: 316 mg, 71%).

$^1$H NMR (400 MHz, CDCl$_3$) δ: 4.07 (s, 2H), 6.77 (s, 1H), 7.07 (d, J=8.0 Hz, 2H), 7.23-7.46 (m, 8H).

(3) N-(Adamantan-2-yl)-4-benzyl-6-phenoxypyrimidine-2-carboxamide (Compound 12)

To 4-benzyl-6-phenoxypyrimidine-2-carbonitrile (32.0 mg, 0.111 mmol) dissolved in tert-butyl alcohol (1.0 mL), a 1 M aqueous sodium hydroxide solution (1.0 mL) was added at room temperature. The mixture was stirred at 110° C. for 1 hour, and the reaction was then terminated by the addition of 2 M hydrochloric acid. The product was subjected to extraction with ethyl acetate (×3). The organic layer was washed with saline, dried over sodium sulfate, and then concentrated to obtain 4-benzyl-6-phenoxypyrimidine-2-carboxylic acid. The obtained compound was dissolved in DMF (1.1 mL). To the solution, 2-adamantanamine hydrochloride (31.3 mg, 0.167 mmol), N,N-diisopropylethylamine (77.3 μL, 0.444 mmol), and HATU (O-(7-azabenzotriazol-1-yl)-N,N,N',N'-tetramethyl uronium hexafluorophosphate) (50.6 mg, 0.133 mmol) were added at room temperature in an argon atmosphere. The mixture was stirred at room temperature for 3 hours, and the reaction was then terminated by the addition of a saturated aqueous solution of sodium bicarbonate. The product was subjected to extraction with ethyl acetate (×3). The organic layer was washed with brine, dried over sodium sulfate, and then concentrated. The residue was purified by TLC for purification (hexane/AcOEt=7/3) to obtain N-(adamantan-2-yl)-4-benzyl-6-phenoxypyrimidine-2-carboxamide (yield: 20.0 mg, 41% from nitrile).

$^1$H NMR (500 MHz, CDCl3) δ: 1.37-1.86 (m, 14H), 4.14 (d, J=9.2 Hz, 1H), 4.23 (s, 2H), 6.66 (s, 1H), 7.10 (d, J=8.0 Hz, 2H), 7.20-7.42 (m, 8H), 8.12 (d, J=9.2 Hz, 1H);

HRMS (ESI): m/z calcd for C$_{28}$H$_{29}$N$_3$O$_2$ [M+H]$^+$ 462.2157, Found 462.2153; HPLC: t$_R$=37.2 min (YMC-Pack ODS-AM); purity: >95% (HPLC analysis at 230 nm).

Test Example 1

Aβ Aggregation Inhibition Test

A test sample solution (solution in DMSO) was added into a 0.1 M phosphate buffer solution (pH 7.4, 50 μL) containing O-acylisopeptide of Aβ (10 μM) (final sample concentration: 30 μM, 1% DMSO), and the mixture was incubated at 37° C. for an arbitrary time. Then, an aliquot (10 μL) of the reaction solution was added to a mixed solution of a thioflavine T solution (50 μM thioflavine T, 10 μL) and a 50 mM glycine-NaOH buffer (pH 8.5, 396 μL) and immediately mixed therewith, and the fluorescence intensity of thioflavine T was measured. In the fluorescence intensity measurement, 440 nm was used as an excitation wavelength, and 480 nm was used as a fluorescent wavelength.

The obtained results are shown in Tables 1 and 2 as an aggregation inhibition ratio when the activity of a DMSO solution used as a control was defined as 100.

TABLE 1

| Compound | Structure | Aggregation inhibition ratio (lower value means stronger inhibitory activity) |
| --- | --- | --- |
| Control | DMSO (control) | 100 |
| Peptide (known) | L-[Lys-Leu-Val-Phe-Phe] (SEQ ID NO: 1) | 107 |
| 1 | 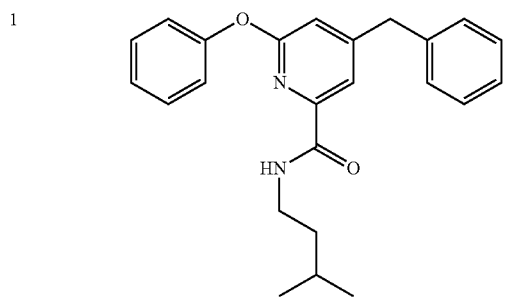 | 61 |

TABLE 1-continued

| Compound | Structure | Aggregation inhibition ratio (lower value means stronger inhibitory activity) |
|---|---|---|
| 2 | (phenoxy-pyridine with naphthylmethyl and isopentyl carboxamide) | 52 |
| 3 | (phenoxy-pyridine with benzyl and isohexyl carboxamide) | 58 |

TABLE 2

| Compound | Structure | Aggregation inhibition ratio (lower value means stronger inhibitory activity) |
|---|---|---|
| 4 | (cyclohexyloxy-pyridine with benzyl and isopentyl carboxamide) | 60 |
| 5 | (benzyloxy-pyridine with benzyl and isopentyl carboxamide) | 75 |

TABLE 2-continued

| Compound | Structure | Aggregation inhibition ratio (lower value means stronger inhibitory activity) |
|---|---|---|
| 6 | (isopentyloxy-pyridine-benzyl with phenethylamide) | 60 |
| 12 | (phenoxy-pyrimidine-benzyl with adamantylmethyl amide) | 40 |

As a result, the compound (1) of the present invention was found to exhibit stronger Aβ aggregation inhibitory activity as compared with the known chain compound.

The invention claimed is:

1. An amide compound represented by the formula (1) or a salt thereof:

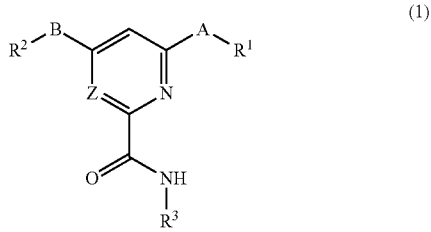

wherein
Z represents CH or N;
A and B are the same or different and each represents —CH$_2$—, —O—, —S—, or —NH—;
R$^1$ and R$^2$ are the same or different and each represents a branched alkyl group, a branched alkenyl group, an optionally substituted aromatic hydrocarbon group, an optionally substituted aralkyl group, an optionally substituted cycloalkyl group, or an optionally substituted aromatic heterocyclic group; and
R$^3$ represents a branched alkyl group, a branched alkenyl group, an optionally substituted cycloalkyl group, or an optionally substituted aralkyl group.

2. The amide compound according to claim 1 or a salt thereof, wherein A and B are the same or different and each is or —CH$_2$— or —O—.

3. The amide compound according to claim 1 or a salt thereof, wherein A is —CH$_2$— or —O—, and B is —CH$_2$—.

4. The amide compound according to claim 1 or a salt thereof, wherein A is —O—, and B is —CH$_2$—.

5. The amide compound according to claim 1 or a salt thereof, wherein R$^1$ and R$^2$ are the same or different and each is a branched alkyl group having 3 to 12 carbon atoms, a branched alkenyl group having 3 to 12 carbon atoms, an optionally substituted aromatic hydrocarbon group having 6 to 14 carbon atoms, an optionally substituted aralkyl group having 7 to 18 carbon atoms, or an optionally substituted cycloalkyl group having 3 to 12 carbon atoms; and R$^3$ is a branched alkyl group having 3 to 12 carbon atoms, a branched alkenyl group having 3 to 12 carbon atoms, an optionally substituted cycloalkyl group having 3 to 12 carbon atoms, or an optionally substituted aralkyl group having 6 to 18 carbon atoms.

6. The amide compound according to claim 1 or a salt thereof, wherein R$^1$ and R$^2$ are the same or different and each is an optionally substituted aromatic hydrocarbon group having 6 to 14 carbon atoms, an optionally substituted aralkyl group having 7 to 18 carbon atoms, or an optionally substituted cycloalkyl group having 3 to 12 carbon atoms; and R$^3$ is a branched alkyl group having 3 to 12 carbon atoms, a branched alkenyl group having 3 to 12 carbon atoms, an optionally substituted cycloalkyl group having 3 to 12 carbon atoms, or an optionally substituted aralkyl group having 6 to 18 carbon atoms.

7. The amide compound according to claim 1 or a salt thereof, wherein R$^1$ and R$^2$ are the same or different and each is a branched alkyl group having 3 to 12 carbon atoms, a branched alkenyl group having 3 to 12 carbon atoms, an optionally substituted aromatic hydrocarbon group having 6 to 14 carbon atoms, an optionally substituted aralkyl group having 7 to 18 carbon atoms, or an optionally substituted cycloalkyl group having 3 to 12 carbon atoms; and R$^3$ is a branched alkyl group having 3 to 12 carbon atoms, a branched alkenyl group having 3 to 12 carbon atoms, an optionally substituted cycloalkyl group having 3 to 12 carbon atoms, or an optionally substituted aralkyl group having 6 to 18 carbon atoms, wherein the group(s) capable of substituting the aromatic hydrocarbon group, the aralkyl group, or the cycloalkyl group is 1 to 5 groups selected from the group consisting of an alkyl group having 1 to 4 carbon atoms, an alkoxy group having 1 to 4 carbon atoms, a hydroxy group, a halogen atom, a nitro group, an amino group, a mono-C$_{1-4}$ alkylamino group, a di-C$_{1-4}$ alkylamino group, and a halogeno-C$_{1-4}$ alkyl group.

8. The amide compound according to claim 1 or a salt thereof, wherein R$^1$ and R$^2$ are the same or different and each is an optionally substituted aromatic hydrocarbon group having 6 to 14 carbon atoms, an optionally substituted aralkyl group having 7 to 18 carbon atoms, or an optionally substituted cycloalkyl group having 3 to 12 carbon atoms; and R$^3$ is a branched alkyl group having 3 to 12 carbon atoms, a branched alkenyl group having 3 to 12 carbon atoms, an optionally substituted cycloalkyl group having 3 to 12 carbon atoms, or an optionally substituted aralkyl group having 6 to 18 carbon atoms, wherein the group(s) capable of substituting the aromatic hydrocarbon group, the aralkyl group, or the cycloalkyl group is 1 to 5 groups selected from the group consisting of an alkyl group having 1 to 4 carbon atoms, an alkoxy group having 1 to 4 carbon atoms, a hydroxy group, a halogen atom, a nitro group, an amino group, a mono-C$_{1-4}$ alkylamino group, a di-C$_{1-4}$ alkylamino group, and a halogeno-C$_{1-4}$ alkyl group.

9. The amide compound according to claim 1 or a salt thereof, which is

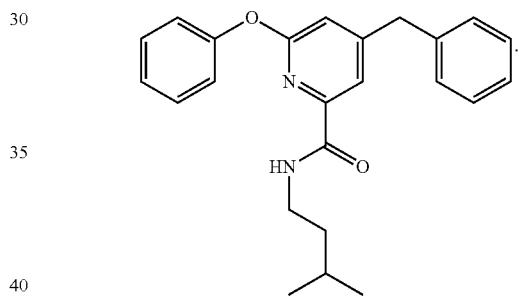

10. The amide compound according to claim 1 or a salt thereof, which is

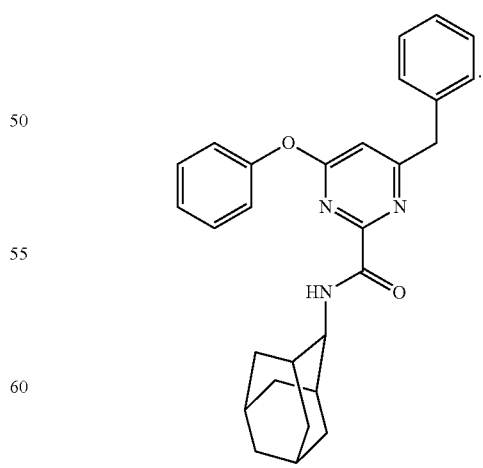

11. A pharmaceutical composition comprising an amide compound according to claim 1 or a salt thereof and a pharmaceutically acceptable carrier.

12. A pharmaceutical composition comprising the amide compound according to claim 2 or a salt thereof and a pharmaceutically acceptable carrier.

13. A pharmaceutical composition comprising the amide compound according to claim 3 or a salt thereof and a phaiiiiaceutically acceptable carrier.

14. A pharmaceutical composition comprising the amide compound according to claim 4 or a salt thereof and a phaiiiiaceutically acceptable carrier.

15. A pharmaceutical composition comprising the amide compound according to claim 5 or a salt thereof and a phaiiiiaceutically acceptable carrier.

16. A pharmaceutical composition comprising the amide compound according to claim 6 or a salt thereof and a pharmaceutically acceptable carrier.

17. A pharmaceutical composition comprising the amide compound according to claim 7 or a salt thereof and a pharmaceutically acceptable carrier.

18. A pharmaceutical composition comprising the amide compound according to claim 8 or a salt thereof and a pharmaceutically acceptable carrier.

19. A pharmaceutical composition comprising the amide compound according to claim 9 or a salt thereof and a pharmaceutically acceptable carrier.

20. A pharmaceutical composition comprising the amide compound according to claim 10 or a salt thereof and a pharmaceutically acceptable carrier.

* * * * *

SEQUENCE LISTING

<160> NUMBER OF SEQ ID NOS: 1

<210> SEQ ID NO 1
<211> LENGTH: 5
<212> TYPE: PRT
<213> ORGANISM: Artificial sequence
<220> FEATURE:
<223> OTHER INFORMATION: peptide

<400> SEQUENCE: 1

Lys Leu Val Phe Phe
1               5